United States Patent [19]
Nielsen et al.

[11] Patent Number: 5,795,320
[45] Date of Patent: Aug. 18, 1998

[54] PAPER APPLICATOR CONTAINING A COMPOSTABLE COATING

[75] Inventors: Steven James Nielsen, Greenville; Yihua Chang, Appleton; Allan James Krueger, Winneconne; Tammy Jo Balzar, Menasha; Richard Roy Tews, Larsen, all of Wis.

[73] Assignee: Kimberly-Clark Worldwide, Inc., Neenah, Wis.

[21] Appl. No.: 696,642

[22] Filed: Aug. 12, 1996

Related U.S. Application Data

[63] Continuation-in-part of Ser. No. 476,481, Jun. 7, 1995, abandoned.

[51] Int. Cl.$^6$ .................................................. A61F 13/20
[52] U.S. Cl. ............................ 604/12; 604/11; 604/14; 604/15
[58] Field of Search ......................... 604/11–18, 285–288

[56] References Cited

U.S. PATENT DOCUMENTS

| | | | |
|---|---|---|---|
| 2,222,088 | 11/1940 | Petersen | 128/263 |
| 2,587,717 | 3/1952 | Fourness | 128/263 |
| 2,922,422 | 1/1960 | Bletzinger | 128/263 |
| 2,922,423 | 1/1960 | Rickard et al. | 128/263 |
| 3,015,332 | 1/1962 | Brecht | 128/263 |
| 3,088,842 | 5/1963 | Kuhnel | 117/7 |
| 3,139,886 | 7/1964 | Tallman et al. | 128/263 |
| 3,390,671 | 7/1968 | Hildebrand | 128/263 |
| 3,429,312 | 2/1969 | Stump | 128/263 |
| 3,462,290 | 8/1969 | Kresse et al. | 117/65.2 |
| 3,581,744 | 6/1971 | Voss et al. | 128/263 |
| 3,724,462 | 4/1973 | Hanke | 128/263 |
| 3,756,238 | 9/1973 | Hanke | 128/270 |
| 3,764,438 | 10/1973 | Voss et al. | 156/425 |
| 3,844,829 | 10/1974 | Black | 117/155 L |
| 3,911,191 | 10/1975 | Guastella et al. | 428/342 |
| 3,954,104 | 5/1976 | Kraskin et al. | 128/263 |

(List continued on next page.)

FOREIGN PATENT DOCUMENTS

| | | | |
|---|---|---|---|
| 860 911 | 1/1971 | Canada | 167/1.5 |
| 0 220 091 A1 | 4/1987 | European Pat. Off. | A61F 13/20 |
| 0 221 424 A1 | 5/1987 | European Pat. Off. | A61F 13/20 |
| 0 551 758 A1 | 7/1993 | European Pat. Off. | A61F 13/26 |
| 0 611 562 A1 | 8/1994 | European Pat. Off. | A61F 13/22 |
| 0 613 672 A1 | 9/1994 | European Pat. Off. | A61F 13/26 |
| 0 699 800 A2 | 3/1996 | European Pat. Off. | D21H 19/28 |
| WO 92/04413 A1 | 3/1992 | WIPO | C08L 67/04 |
| WO 94/07941 | 4/1994 | WIPO | C08J 5/18 |
| WO 94/08090 | 4/1994 | WIPO | D21H 19/28 |
| WO 94/15718 A2 | 7/1994 | WIPO | B05C 5/02 |

OTHER PUBLICATIONS

American Society for Testing and Material (ASTM) Designation: D 1894—90, "Standard Test Method for Static and Kinetic Coefficients of Friction of Plastic Film and Sheeting," pp. 116–120.

Higdon, Archie, William B. Stiles, Arthur W. Davis, and Charles R. Evces, "Coefficient of Friction," SI Version, *Engineering Mechanics*, Second Vector Edition, vol. I: Statics, 1976, Prentice–Hall, Inc., p. 206.

Patent Cooperation Treaty Search Report from the International Search Authority, International Application No. PCT/US 96/08915 dated Jan. 15, 1997.

*Primary Examiner*—John G. Weiss
*Assistant Examiner*—Dennis Ruhl
*Attorney, Agent, or Firm*—Thomas J. Connelly

[57] ABSTRACT

An applicator is disclosed for inserting a substance into a body cavity. The applicator is especially useful for inserting a catamenial tampon into a woman's vagina. The applicator includes a tubular member formed from at least one layer of paper which has an exterior surface. The tubular member is capable of holding the substance which is to be inserted. The exterior surface of the tubular member is coated with a compostable coating. The coating is comprised of at least 85 percent by weight of a polymeric material, at least 10 percent by weight of additives, and up to about 5 percent by weight of a residual monomer.

24 Claims, 4 Drawing Sheets

U.S. PATENT DOCUMENTS

| | | | |
|---|---|---|---|
| 4,076,895 | 2/1978 | Theno | 428/516 |
| 4,082,877 | 4/1978 | Shadle | 428/35 |
| 4,337,721 | 7/1982 | Varga | 118/60 |
| 4,388,349 | 6/1983 | Korpman et al. | 427/208.4 |
| 4,412,833 | 11/1983 | Wiegner et al. | 604/14 |
| 4,415,610 | 11/1983 | Choinski | 427/372.2 |
| 4,453,925 | 6/1984 | Decker | 604/14 |
| 4,490,418 | 12/1984 | Yoshida | 427/445 |
| 4,503,098 | 3/1985 | Potts | 427/394 |
| 4,600,404 | 7/1986 | Sheldon et al. | 604/387 |
| 4,675,208 | 6/1987 | Kageyama et al. | 427/128 |
| 4,792,326 | 12/1988 | Tews | 604/11 |
| 4,805,554 | 2/1989 | McIntyre | 118/666 |
| 4,822,640 | 4/1989 | Tuhkanen et al. | 427/211 |
| 4,828,770 | 5/1989 | Fabian et al. | 264/40.3 |
| 4,883,691 | 11/1989 | McIntyre | 427/434.2 |
| 5,032,433 | 7/1991 | Isayev et al. | 428/1 |
| 5,142,023 | 8/1992 | Gruber et al. | 528/354 |
| 5,165,941 | 11/1992 | Hawley | 425/148 |
| 5,173,119 | 12/1992 | Watanabe et al. | 118/410 |
| 5,185,010 | 2/1993 | Brown, Jr. | 604/379 |
| 5,219,646 | 6/1993 | Gallagher et al. | 428/287 |
| 5,252,369 | 10/1993 | Akao et al. | 428/34.9 |
| 5,302,206 | 4/1994 | Shibata et al. | 118/410 |
| 5,346,468 | 9/1994 | Campion et al. | 604/13 |
| 5,389,067 | 2/1995 | Rejai | 604/14 |
| 5,436,030 | 7/1995 | Damrau | 427/240 |
| 5,520,958 | 5/1996 | Doesburg et al. | 427/316 |
| 5,547,701 | 8/1996 | Nielsen et al. | 427/2.3 |

PAPER APPLICATOR CONTAINING A COMPOSTABLE COATING

This application is a continuation-in-part of application Ser. No. 08/476,481, entitled "Paper Applicator Containing a Compostable Coating" and filed in the U.S. Patent and Trademark Office on Jun. 7, 1995, now abandoned. The entirety of this application is hereby incorporated by reference.

FIELD OF THE INVENTION

This invention relates to a coated paper applicator for inserting a substance into a body cavity and an apparatus and method of forming the applicator. More specifically, this invention relates to a paper applicator having a compostable coating on an exterior surface which provides the applicator with a low coefficient of friction.

BACKGROUND OF THE INVENTION

Today, many different types of applicators exist which are used to insert a substance into a body cavity. A common applicator is a tampon applicator which is used by women to insert a tampon pledget into their vagina during their menstrual period. Other common applicators are used to insert suppositories, creams or the like to the vaginal area or into other body cavities.

Tampon applicators are commonly constructed of either a water-insoluble plastic, such as polyethylene, or from multiple layers of paper, paperboard or cardboard. The plastic applicators can be injection molded and are preferred by certain women because of their smooth and slippery exterior surface which provides ease and comfort during insertion. The plastic applicators can present a disposal problem in that they should not be flushed down a toilet but instead disposed of with the dry trash. Plastic applicators further raise environmental concerns in that some plastics are slow to biodegrade and most are not compostable.

Paper applicators, on the other hand, are flushable and exhibit good biodegradability features. The flushable feature is highly desired by most women for it provides a discreet means of disposing of the used applicator. However, most of today's paper applicators are not as comfortable to insert as a plastic applicator. In addition, paper applicators usually do not exhibit the sleek and lustrous aesthetic appearance of a plastic applicator. Even when the exterior surface of a paper applicator is coated, it lacks the characteristic of being slippery and does not have the low coefficient of friction feature exhibited by plastic applicators. Furthermore, many paper applicators are coated with a non-compostable coating.

Now a paper tampon applicator has been invented which has a compostable coating on its exterior surface, which closely approximates the aesthetic appearance of a plastic applicator and which has a lower coefficient of friction than a plastic applicator.

SUMMARY OF THE INVENTION

Briefly, this invention relates to a paper applicator for inserting a substance into a body cavity and an apparatus and method of forming the applicator. The applicator is especially useful for inserting a catamenial tampon into a woman's vagina. The applicator includes an elongated tubular member formed from at least one layer of paper which has an exterior surface. The tubular member is capable of holding the substance which is to be inserted. The exterior surface of the tubular member is coated with a compostable coating which is comprised of at least 85 percent by weight of a polymeric material, at least 10 percent by weight of additives, and up to about 5 percent by weight of a residual monomer. The coating provides the tubular member with a dry coefficient of kinetic friction ranging from between about 0.62 to about 0.86 and a wet coefficient of kinetic friction ranging from between about 0.59 to about 1.12. The low dry and wet coefficient of friction values facilitate insertion of the applicator into the body cavity.

The general object of this invention is to provide a paper applicator containing a compostable coating for inserting a substance into a body cavity. A more specific object of this invention is to provide a paper tampon applicator having a compostable coating formed on an exterior surface thereof which provides the applicator with a low coefficient of friction.

Another object of this invention is to provide a tampon applicator formed from a single layer of paper and having an external coating which reduces friction during insertion of the applicator into a woman's vagina.

A further object of this invention is to provide a paper applicator with a coating which provides the applicator with a low coefficient of friction in both a wet and a dry state.

Still another object of this invention is to provide a coated paper applicator which is more comfortable to use.

Still another object of this invention is to provide an apparatus which can coat a layer of paper efficiently and economically.

Still further, an object of this invention is to provide a paper applicator with a polylactide coating which contains a lactide monomer, a nucleating agent, an anti-oxidant or stabilizer, a plasticizer, an anti-blocking agent, a slip agent and a water scavenger.

Still further, an object of this invention is to provide a method of coating the exterior paper layer and shaping the paper into a tubular member.

Other objects and advantages of the present invention will become more apparent to those skilled in the art in view of the following description and the accompanying drawings.

DETAILED DESCRIPTION OF THE PREFERRED EMBODIMENTS

Figure 1:
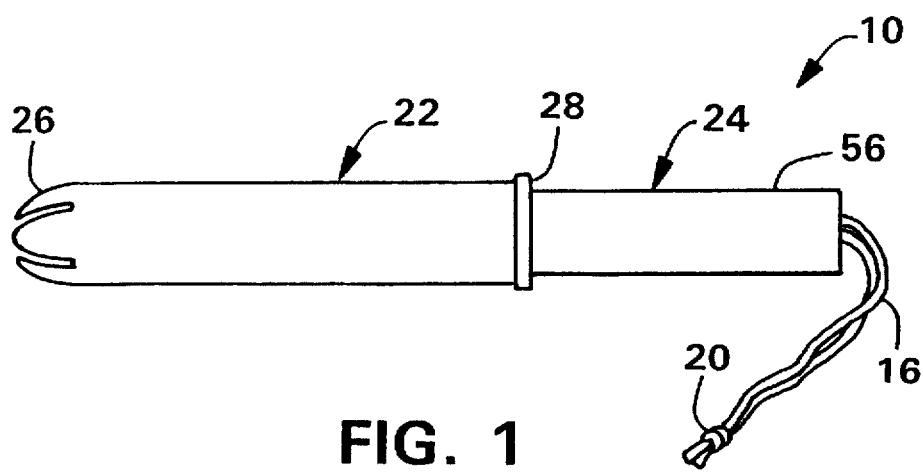
FIG. 1 is a side elevational view of a paper applicator having a compostable coating on the exterior surface thereof.
Figure 2:
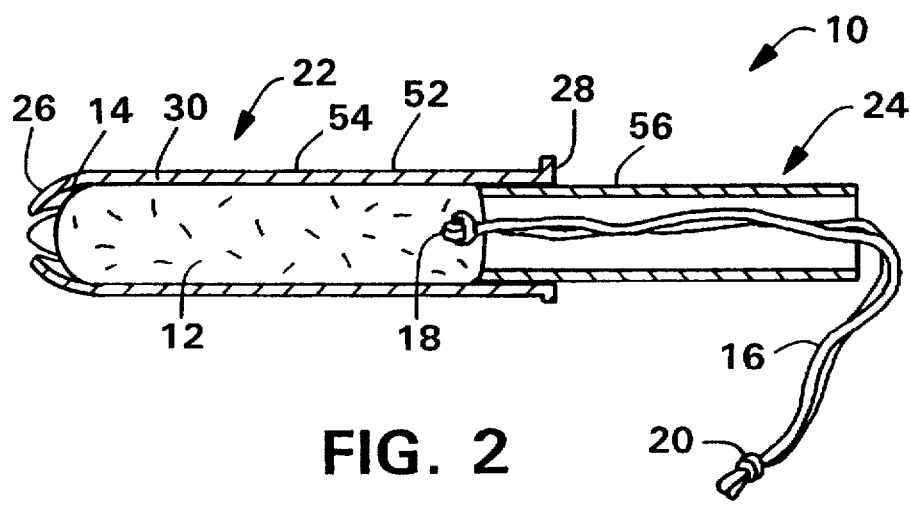
FIG. 2 is a cross-sectional view of the paper applicator shown in FIG. 1 depicting the presence of a tampon and showing the telescopic assembly of the inner and outer tubes.

Referring to FIGS. 1 and 2, an applicator 10 is shown which is capable of dispensing a substance into a body cavity. A "substance" is defined as that which has mass and occupies space. A substance can be a physical structure such as a tampon, a capsule such as a suppository, or medication in the form of an ointment, a gel, a cream, a solid, etc. For the purpose of discussion, the applicator 10 is depicted in the form of a tampon applicator which is designed to house a catamenial tampon 12 and provide a comfortable means for inserting the tampon 12 into a woman's vagina.

Although this invention will be described with reference to a tampon applicator, it should be recognized that the applicator 10 can be used to insert suppositories or to dispense medication, such as a yeast infection ointment, creams or the like into the vaginal area of a woman. The applicator 10 can also be used to dispense some other substance into a body cavity or onto the skin of a human or an animal.

A tampon is an absorbent member primarily designed to be worn by a woman during her menstrual period to absorb menses, blood and other body fluids. The tampon 12 can be made from natural or synthetic fibers, including cellulose fibers such as cotton or rayon, or artificial fibers such as polyester, polypropylene, nylon or blends thereof. A blend of cotton and rayon fibers works well. Other types of material may also be used, such as a cellulose sponge or a sponge formed from elastomeric materials.

The tampon 12 is normally compressed into the form of a cylinder and can have a blunt, rounded or nose-shaped forward end 14. The tampon 12 commonly has a withdrawal string 16 fastened to an end thereof which serves as a means for withdrawing the soiled tampon from the woman's vagina. The withdrawal string 16 can be looped through an aperture 18 formed transversely through the tampon 12. In addition, the withdrawal string 16 can have a knot 20 formed at its free end to assure that the string 16 will not separate from the tampon 12.

The applicator 10 includes a first member 22 and a second member 24. The first member 22 is commonly referred to as an outer tube and is in the form of an elongated hollow tube which is sized and configured to hold and temporarily retain a substance, i.e., a tampon 12, which is to be inserted into the body cavity. The first member 22 can be straight or curved along its length. The second member 24 is commonly referred to as an inner tube or plunger and can be either in the form of a solid stick or an elongated hollow tube. The second member 24 can be telescopically slidable within the first member 22 and is designed to expel the tampon 12 from the first member 22 as it is moved into the outer tube 22. The second member 24 can be straight or curved along it's length.

It should be noted that although the applicator 10 is depicted as a pair of interacting telescopic members, it can consist of a single tubular member wherein the user will utilize one of her fingers or an independent plunger to expel a substance from the tubular member into the body cavity.

The first member 22 of the applicator 10 has first and second spaced apart ends 26 and 28, respectively. The first member 22 is shown being formed from a single ply or layer of material 30. The layer 30 can be made from paper, paperboard, cardboard or a combination thereof. The words "paper, paperboard and cardboard" are used herein to mean a thin sheet material made from cellulose pulp which is derived mainly from wood, rags and certain plants, including leaves and grasses. Although the first member 22 can consist of a single layer or ply of material 30, which is rolled, spirally wound, convolutely wound or longitudinally seamed into a hollow, tubular configuration, it is also possible to employ two or more layers, especially where rigidity is of concern.

It should be noted that when two or more layers are present, that different materials can be employed for each layer, if desired. The thickness of the single ply 30 should range from between about 0.0055 inches to about 0.015 inches (about 5.5 mils to about 15 mils), preferably, between about 0.008 inches to about 0.013 inches (about 8 mils to about 13 mils), and most preferably, about 0.01 inches (about 10 mils).

Figure 3:
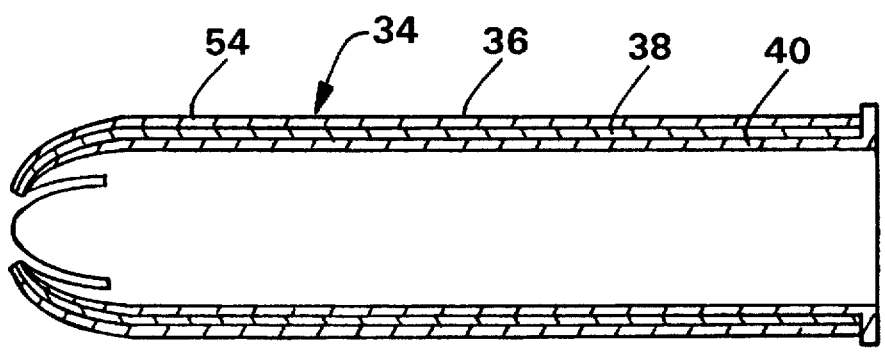
FIG. 3 is an enlarged cross-sectional view of a tubular applicator constructed from three layers of paper and having a compostable coating on the exterior surface of the outer paper layer.

Referring to FIG. 3, an alternative embodiment of an applicator 32 is shown wherein a tubular member 34 is constructed of three separate and distinct plies or layers of paper, paperboard or cardboard material 36, 38 and 40. The plies 36, 38 and 40 can be made from the same, similar or different materials and each can have the same, similar or different properties. For example, each ply 36, 38 and 40 can have a similar or different board weight, thickness, density, etc. The paper, paperboard and cardboard plies 36, 38 and 40 must be capable of supplying the required rigidity to the applicator 32 for its intended purpose. The thickness of each inner ply 38 and 40 should range from about 0.002 inches to about 0.007 inches (about 2 mils to about 7 mils), and preferably the thickness will be about 0.004 inches (about 4 mils). The outer paper ply 36 should have a thickness of between about 0.0015 inches to about 0.005 inches (about 1.5 mils to about 5 mils), preferably between about 0.0015 inches to about 0.002 inches (about 1.5 mils to about 2 mils), and most preferably, about 0.0016 inches (about 1.6 mils). The overall wall thickness of the paper plies 36, 38 and 40 will range between about 0.0055 to about 0.0155 inches (about 5.5 mils to about 15.5 mils), preferably, about 0.01 inches (about 10 mils).

Figure 4:
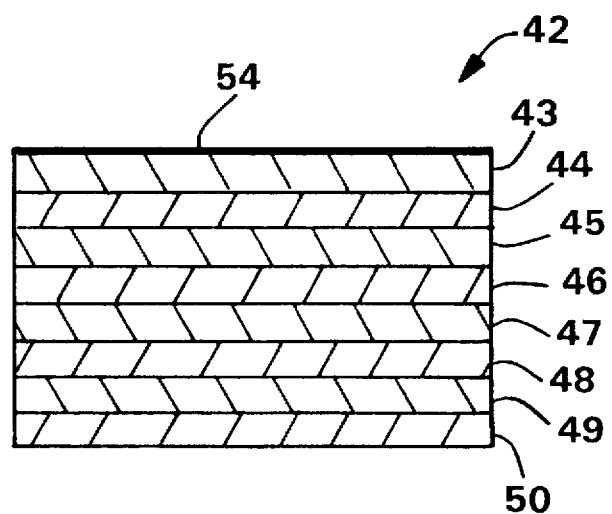
FIG. 4 is a cross-sectional view of a portion of the tubular wall of an applicator constructed of eight layers of paper and having a compostable coating on the exterior surface of the outer paper layer.

Referring to FIG. 4, a third embodiment is shown wherein a wall portion 42 of an applicator is constructed of eight separate and distinct plies or layers of materials 43, 44, 45, 46, 47, 48, 49 and 50. Any number of plies between one and eight can be utilized with three to five plies being preferred. The use of fewer layers helps to reduce the overall cost of the applicator 10 and significantly simplifies the manufacturing process. It is also advantageous to use an inexpensive groundwood paper for the interior plies and to use a thinner and more refined paper for the exterior ply. The groundwood paper should have a greater thickness and board weight than the exterior paper layer because its purpose is to add rigidity and stiffness to the applicator at a nominal cost.

The various plies or layers used to form the tubular applicator 32 or 42 can be rolled, spirally wound, convolutely wound or longitudinally seamed into a hollow tubular member 34 or 42. The individual plies 36, 38 and 40 or 43-50 can be glued together with an adhesive to retain the tubular shape. The adhesive should be a water-soluble adhesive, so as to allow the different plies to delaminate when the applicator 32 or 42 is exposed to water. This will facilitate disposal of the applicator 32 or 42 by allowing it to be flushed down a toilet. A water-based adhesive also enhances the biodegradability of the paper applicator 32 or 42. Suitable adhesives include polyvinyl acetate and dextrin, with polyvinyl acetate being preferred because of its ability to resist delamination under humid storage conditions. Suitable polyvinyl acetate adhesives are commercially available from National Starch Company, having an office at 10 Finderne Avenue, P.O. Box 6500, Bridgewater, N.J. 08807.

When forming the wall of the tubular member 34 or 42, it is preferred that the seam formed in each ply or layer during winding be offset from the seams formed in adjacent plies. Furthermore, in order to reduce cost, the inexpensive inner plies 38 and 40 or 44–50 can be formed from a durable, groundwood paper while the outer plies, 36 and 43 respectively, in the two different embodiments, can be formed from a bleached Kraft paper, a bleached sulfite paper or a thinner sheet of groundwood having a relatively smooth surface. The outer paper layer 36 or 43 should be formed from a white paper. A high degree of whiteness enhances the aesthetic appearance of the applicator. The outer paper layer 36 or 43 should also exhibit high strength and should be generally stiffer than any of the inner plies. The reason for this is that the outer paper layer 36 or 43 must have sufficient strength to allow a coating to be applied thereto and to be rewound wrinkle free.

Referring again to FIGS. 1 and 2, the layer of material 30 which forms the first member 22 has an exterior surface 52. This exterior surface 52 is covered with a compostable coating 54. By "compostable" is meant that the coating will compost out in a compost bin and will not release harmful by-products. As the coating degrades, it produces carbon dioxide ($CO_2$), water and humus. The polylactide coating needs moisture and bacteria to degrade. The coating 54 is also biodegradable. By "biodegradable" is meant that the coating is capable of being decomposed by natural biological processes. *The Random House Dictionary of the English Language*, Second Edition Unabridged, copyrighted 1987 defines "biodegradable" on page 209 as "capable of decaying through the action of living organisms." Furthermore, the coating is water resistant. By "water resistance" is meant the coating is resisting, though not entirely preventing, the penetration of water. Since the coating 54 is applied to the exterior surface 52 as a very thin layer, the applicator 10 can be disposed of by flushing down a toilet. The thin layer of coating 54 will not prevent the paper layer 30 from breaking apart in water but may increase the time needed for this to occur.

The coating 54 can be applied to the paper layer 30 before, during or after the material is rolled or wound into the tubular configuration. Preferably, the coating 54 is applied to the paper layer 30 before it is rolled, wound or seamed into a tubular member. The coating 54 can be applied to the exterior surface 52 by spraying, melt spraying, extrusion, slot coating, screen printing or by using other methods known to those skilled in the art. Slot coating is one method that works especially well for it allows a very thin, uniform coating to be applied at reasonable production speeds. For this invention, it is critical that the coating 54 be applied such that it is very thin and uniform. The reason for this is that a very thin coating will reduce the cost of the finished applicator 10, allow any petals which may be formed on the insertion end of the applicator 10 to flex under reasonable force, and will not prevent the applicator 10 from breaking apart in water. The uniform coating is advantageous in that it facilitates obtaining both the wet and dry, low coefficient of friction values.

The coating 54 is comprised of at least 85 percent by weight of a polymeric material, at least 10 percent by weight of additives, and up to about 5 percent by weight of a residual monomer. A preferred polymeric material is polylactide with the residual monomer being a lactide monomer. Polylactide is available from Cargill Incorporated having an office at 15407 McGinty Road, Wayzata, Minn. 55391-2399. Polylactides identified by code numbers 520HR and 520HRXC work well. The polylactide has a molecular weight ranging from between about 100,000 to about 300,000.

The residual monomer is present in amounts up to about 5 percent but no monomer need be present if it can be removed from the polymer. Usually, from about 0.1 to about 5 percent by weight of a residual monomer will be present. The less monomer present, the better. The residual monomer can be a lactide monomer when the polymeric material is polylactide. Lactide monomer is a lactide acid or dimer of lactide acid. When one polymerizes polylactide, some residual monomer will normally be present in the finished polymer. The technology available today for polymerizing a material normally produces a polymer with up to about 5 percent by weight of a monomer. If one wishes to reduce the level of monomer left in the finished polymer to below about 5 percent by weight, one would have to utilize additional process steps or carry out the process under more stringent conditions. Either alternative is costly to implement and usually requires additional equipment and/or time. The reduction of the residual monomer below the range of from about 0.1 to about 5 percent by weight is not easy. It is important to this invention that one minimizes the amount of residual monomer which remains after polymerization to less than about 5 percent by weight, preferably, less than about 4 percent by weight, and most preferably, less than about 3 percent by weight.

The polylactide coating of this invention also contains the following additives: a nucleating agent, an anti-oxidant or stabilizer, a plasticizer, an anti-blocking agent, a slip agent and a water scavenger. It is important that all six of these additives be present. The reasons for including these additives and the amounts of such additives are described below. The nucleating agent must be present for it increases crystallization kinetics of the polylactide. It is well known that polylactide crystallizes very slowly, normally in a time period of several hours or even days. Therefore, the addition of a nucleation agent is required to allow the polylactide coating to set up quickly once it is applied onto a paper substrate in a high speed commercial process. The nucleating agent should be present in an amount ranging from between about 1 to about 5 percent by weight, preferably about 3 percent by weight, and most preferably, about 2 percent by weight. A nucleating agent which works well is adipic acid.

The second additive is the anti-oxidant or stabilizer. The anti-oxidant is added to the polylactide polymer because it is beneficial in reducing degradation caused by high temperatures during processing, thus preventing the coating from discoloring or turning yellow. It is preferable that the coating be clear, not opaque. Since polylactide is extremely vulnerable to thermal degradation, it is extremely important that an anti-oxidant be present. The anti-oxidant should be present in an amount ranging from between about 1 to about 5 percent by weight, preferably less than about 3 percent by weight, preferably less than about 2 percent by weight. Examples of two commercially available anti-oxidants are sold under the trademarks "ULTRANOX" AND "IRGANOX". ULTRANOX® is sold by GE Specialty Chemicals, Inc. having an office at Parkersburg Center, 5th & Avery Streets, Parkersburg, W.V. and IRGANOX® is sold by Ciba-Geigy Corporation having an office in Ardsley, N.Y.

The third additive is the plasticizer. The plasticizer is needed to reduce the melt viscosity of the polylactide polymer so that it has better flow characteristics and is easier to extrude from a commercial extruder. The plasticizer also enables the coating to exhibit a flexibility such that after being coated onto a paper substrate, the paper substrate can be worked into various geometric configurations without having the coating deform, i.e. crack, exhibit stress fractures, etc. The plasticizer should be present in an amount ranging from between about 6 to about 15 percent by weight, preferably from between about 6 to about 12 percent by weight, and most preferably, from between about 6 to about 10 percent by weight. An example of a commercially available plasticizer is sold under the trademark "CITROFLEX" A-4 by Morflex, Inc. of Greensboro, N.C.

The fourth additive is the anti-blocking agent. The anti-blocking agent is added to the polylactide polymer to prevent the coating from adhering to itself or another substrate. For example, the anti-blocking agent will prevent the coating from sticking to the back side of a coated paper after the paper has been rolled up into a supply roll. The anti-blocking agent should be present in an amount ranging from between about 0.5 to about 10 percent by weight, preferably from between about 2 to about 9 percent by weight, and most preferably, from between about 3 to about 8 percent by weight. An example of a commercially available anti-blocking agent is sold under the trademark ULTRATALC® by Minerals Technologies Inc. having an office at 235 E. 42nd Street, New York, N.Y.

The fifth additive is the slip agent. The slip agent is needed to reduce the wet and dry coefficient of friction values of the polylactide coating. The slip agent is capable of migrating to the surface of the coating and thereby lowers both the wet and dry, coefficient of friction values. The plasticizer should be present in an amount ranging from between about 1 to about 10 percent by weight, preferably from between about 2 to about 10 percent by weight, and most preferably, from between about 3 to about 10 percent by weight. An example of a commercially available slip agent is erucamide sold under the trademark ARMOSLIP® by AKZO having an office at 300 S. Riverside Plaza, Chicago, Ill. 60175.

The last additive is the water scavenger. The water scavenger is needed to prevent hydrolysis of the polylactide. This is accomplished by having the water scavengers molecularly bond with the water molecules thereby preventing the water from interacting with the polymer. The water scavenger should be present in an amount ranging from between about 0.5 to about 5 percent by weight, preferably from between about 0.5 to about 3 percent by weight, and most preferably, from between about 0.5 to about 2 percent by weight. An example of a commercially available water scavenger is under the trademark "STABAXOL" by Bayer AG having an office in Leverkusen, Germany.

The coating 54 is directly bonded to the exterior surface 52 of the paper layer 30 which forms the first member 22. One method is to slot coat a continuous hot liquid stream of a thermoplastic resin onto the outer paper layer 30. This action causes the coating 54 to thermally adhere to the surface 52 of the paper layer 30 as it cools. Once cooled to room temperature, it is essentially impossible to separate the coating 54 from the paper layer 30 without removing cellulose fibers from the paper layer 30.

When the coating 54 is applied to an applicator which is to be used as a tampon applicator, it is critical that the coating has a uniform thickness. By "uniform thickness" is meant that the coating has a thickness which varies by no more than ±25 percent over the surface to which it is applied. Preferably, the thickness of the coating 54 will not vary by more than ±20 percent over the exterior surface 52 to which it is applied, and most preferably, the thickness of the coating 54 will not vary by more than ±15 percent over the exterior surface 52 to which it is applied.

It should be noted that the thickness of the coating described above relates to the exterior surface 52 of the applicator 10. However, the coating can also be applied to an interior surface and, when so applied, it is also important that the coating be applied so that it has a uniform thickness. A uniform thickness will allow the tampon 12 to be expelled from the applicator 10 at a low expulsion force.

For a tampon applicator constructed from one or more layers of paper, the coating 54 should be very thin. It is important that the coating 54 have a thickness of between about 0.3 mils to about 1.0 mils. Preferably, the coating 54 will have a thickness of between about 0.4 mils to about 0.6 mils, and most preferably, the thickness of the coating 54 will be about 0.5 mils. It is critical that the coating have a thickness of less than about 1.0 mils in order to keep the cost down and to ensure that the coating has sufficient thickness to accomplish the purpose for which it was applied.

In the coating art, the thickness of a coating is typically referred to in "mils." One mil is equal to 0.001 inches. Therefore, the overall thickness of a coated applicator, where a single layer of paper 30 with a thickness of between about 0.0055 inches to about 0.0165 inches (about 5.5 mils to about 16.5 mils) is coated with a material, i.e., a film coating, having a thickness of between about 0.003 inches to about 0.010 inches (about 3 mils to about 10 mils), will produce an applicator having a thickness of between about 0.0085 inches to about 0.0265 inches (about 8.5 mils to about 26.5 mils). For a three layered applicator as depicted in FIG. 3, wherein the thickness of all three layers ranges from between about 0.0055 inches to about 0.0165 inches (about 5.5 mils to about 16.5 mils) and the thickness of the coating is between about 0.003 inches to about 0.010 inches (about 3 mils to about 10 mils), will produce an applicator having an overall thickness of between about 0.0085 inches to about 0.0265 inches (about 8.5 mils to about 26.5 mils) as well. For a multiple layer applicator as shown in FIG. 4, the overall thickness of the applicator 42, paper layers plus coating, can be greater than about 0.0265 inches (about 26.5 mils).

The first function of the coating 54 is to give the applicator 10 a pleasing aesthetic appearance. From an aesthetic viewpoint, the coating 54 must make the outer surface of the applicator smooth and convey a slippery, satin texture. The composition of the coating 54 should be such that its smoothness will not be degraded by humidity, i.e., it should not become tacky to the touch. The smoothness characteristic is extremely important for it directly relates to the ease and comfort a woman experiences when she inserts the tampon applicator into her vagina and then withdraws the tampon applicator from her vagina. The smoothness of a particular coating can be measured a number of different ways. The more common ways of measuring smoothness of a material is to measure the surface parameters, such as the dry and wet coefficient of kinetic frictions or by scanning the surface smoothness using electron microscopy, contact angle, etc.

A second function of the coating 54 is that it should provide the paper layer 30 with a shininess or sheen so that it takes on a satiny or lustrous appearance. The appearance should be similar to that of a plastic applicator.

A third function of the coating 54 is that it should provide the first member 22 with a low coefficient of friction. "Coefficient of friction (COF)," as used herein and as generally defined, is a measure of the relative difficulty when the surface of a first material slides over the surface of itself or over the surface of a second material. For our purposes, we are concerned with the coefficient of kinetic friction when one surface is moved relative to a second surface. The coefficient of kinetic friction is usually lower than the coefficient of static friction. A high COF denotes low slip between two contacting surfaces while a low COF denotes a high slip between two contacting surfaces. A low COF is desirable when an applicator is inserted into and/or removed from a body cavity.

A standard test procedure which can be used to measure the coefficient of kinetic friction of a particular coating is described in "The American Society for Testing and Materials" (ASTM) D 1894–90. This test procedure is entitled: "STANDARD TEST METHOD FOR STATIC AND KINETIC COEFFICIENTS OF FRICTION OF PLASTIC FILM AND SHEETING." The samples to be tested should be acclimated for approximately two hours before being tested in a controlled environment of 23° C.±1° C. (73.4° F.±1.8° F.) and a relative humidity of 50±2 percent. The coefficient of kinetic friction test should follow the above-identified ASTM procedure with the following exceptions. First, a porcelain plate is positioned over the metal sheet forming the "plane" on which the sled is moved. This change is made so that the friction measurements can also be used to simulate a situation where a coated tampon applicator is flushed down a toilet. The surface of a toilet is porcelain and the use of a porcelain surface on the sled will more closely simulate actual conditions. The lower the COF value, the easier it will be for the applicator to flow through the toilet traps and sewer pipes. A test was conducted to determine the "dry coefficient of kinetic friction (COF)" value of a single layer of groundwood coated with a polylactide coating, as described above. By "dry COF" is meant that the samples were tested according to the ASTM D 1894 procedure without being wetted by a liquid.

The groundwood had a thickness of about 0.0025 inches (about 2.5 mils) and the polylactide coating had a uniform thickness of about 0.005 inches ±25% (about 5 mils ±25%). Each sample was sized 2.5 inches by 4.5 inches (63.5 mm by 114.3 mm). Each test sample was sequentially attached to the 2.5 inch square (63.5 mm by 63.5 mm) sled by two-sided tape and the excess material was wrapped around the sides and top surface of the sled in the cross direction. The 2.5 inch (63.5 mm) dimension was in the machine direction (MD) and the 4.5 inch (114.3 mm) dimension was in the cross or transverse direction (CD). It should be noted that the coating was applied to each sample in the machine direction.

Each test sample was measured for its dry coefficient of kinetic friction value and the results were displayed as a line on a chart recorder. This line was then arbitrarily divided by five equally spaced vertical lines into six equal parts. The values at each of the five vertical lines were averaged to obtain a single data point. Five locations were picked so as to give a more representative measurement for each test sample over its distance of travel. Each data point was referred to as a dry COF and the results are listed in Table 1 below. A total of 25 test samples was measured.

A second test was conducted to determine the "wet coefficient of kinetic friction (COF)" value of a single layer of groundwood coated with a polylactide coating as described above. By "wet COF" is meant that the samples were tested in the presence of deionized water. The deionized water had an electrical resistance of 18 MW (megaohms) and a surface tension of 70.8 dynes per centimeter. In order to run this test, a dam was formed from caulking material placed around the outer perimeter of the porcelain plate. The dam had a vertical height of approximately a half of an inch (12.7 mm). The dam enclosed a rectangular area of about 12.5 inches by about 6 inches (about 317.5 mm by about 152.4 mm). Approximately 90±5 milliliters of deionized water was then poured onto the porcelain plate such that it completely wetted the porcelain plate. Each sample was then sequentially tested using the methodology described above and the results are listed in Table 1 below. A total of 25 test samples was measured.

A third and a fourth test were conducted to determine the dry and wet coefficient of kinetic friction values of samples of "PLAYTEX" "SILK GLIDE". "PLAYTEX" "SILK GLIDE" is a commercially available paper tampon applicator sold by Playtex Family Products Corporation of Stamford, Conn. This paper applicator is constructed of two plies of paper with a two layer film coating applied to the outer paper layer. The coating consists of an inner layer of polyethylene film having a thickness of about 0.5 mils and an outer layer of polyester film having a thickness of about 0.5 mils. The "PLAYTEX" paper applicator was unwound, starting from the longitudinal seam, onto a planar sheet and the two layer film was then separated from the outer paper layer. The film was then attached to the 2.5 inch square (63.5 mm by 63.5 mm) sled with the outer polyester film layer facing the porcelain surface. Each sample was tested for dry COF and wet COF as indicated above and the results are listed in Table 1 below. A total of 25 test samples was measured for dry COF and wet COF.

TABLE 1

| SAMPLE | DRY PLA | DRY SILK GLIDE | WET PLA | WET SILK GLIDE |
|---|---|---|---|---|
| 1 | 0.62 | 0.43 | 0.69 | 0.79 |
| 2 | 0.64 | 0.46 | 0.85 | 0.83 |
| 3 | 0.64 | 0.40 | 0.76 | 0.94 |
| 4 | 0.66 | 0.44 | 0.82 | 0.87 |
| 5 | 0.73 | 0.41 | 0.83 | 0.87 |
| 6 | 0.70 | 0.40 | 0.95 | 0.91 |
| 7 | 0.74 | 0.43 | 0.89 | 0.94 |
| 8 | 0.71 | 0.42 | 1.02 | 0.91 |
| 9 | 0.72 | 0.43 | 0.91 | 1.05 |
| 10 | 0.69 | 0.41 | 0.88 | 0.99 |
| 11 | 0.73 | 0.46 | 0.93 | 0.95 |
| 12 | 0.77 | 0.44 | 1.04 | 0.94 |
| 13 | 0.86 | 0.47 | 1.07 | 1.04 |
| 14 | 0.80 | 0.43 | 1.06 | 1.02 |
| 15 | 0.84 | 0.44 | 1.04 | 0.95 |
| 16 | 0.83 | 0.45 | 0.98 | 0.93 |
| 17 | 0.78 | 0.45 | 1.03 | 0.97 |
| 18 | 0.72 | 0.45 | 1.08 | 1.01 |
| 19 | 0.79 | 0.48 | 1.02 | 0.94 |
| 20 | 0.79 | 0.43 | 1.05 | 1.10 |
| 21 | 0.81 | 0.45 | 1.08 | 1.14 |
| 22 | 0.82 | 0.51 | 1.12 | 1.00 |
| 23 | 0.80 | 0.49 | 1.10 | 1.09 |
| 24 | 0.80 | 0.48 | 0.93 | 1.08 |
| 25 | 0.77 | 0.42 | 0.92 | 0.89 |
| Average | 0.75 | 0.44 | 0.96 | 0.96 |
| Std Dev. | 0.07 | 0.03 | 0.11 | 0.07 |

Note:
1. "PLA" is an abbreviation for polylactide.
2. "Std Dev." is an abbreviation for Standard Deviation.

The above test data indicates that the polylactide coating 54 provided the applicator with both a low, dry coefficient of kinetic friction value and a low, wet coefficient of kinetic friction value. The dry COF values for the polylactide coating 54 ranged from between 0.62 to 0.86. It is critical to this invention that the dry COF value should be less than about 0.80, and more preferably, the dry COF value should be less than about 0.75.

The wet COF values for the polylactide coating 54 ranged from between 0.69 to 1.12. It is critical to this invention that the wet COF values should be less than about 1.0, and more preferably, less than about 0.96. These low dry and wet COF values facilitate insertion and removal of the applicator into and out of a body cavity.

The above test data also indicates that the two layer "PLAYTEX" "SILK GLIDE" coating of polyester/polyethylene provided the applicator with both a low, dry coefficient of kinetic friction value and a low, wet coefficient of kinetic friction value. The dry COF values for the polyester coating ranged from between 0.40 to 0.51. The wet COF values ranged from between 0.79 to 1.14. Although the dry and wet COF values overlap the dry and wet coefficient of kinetic friction values of the present invention, one should note that the coatings are different. First, our inventive coating is compostable while the "PLAYTEX" "SILK GLIDE" coating is not. Second, our inventive coating is a single layer film while the "PLAYTEX" "SILK GLIDE" coating is a two layer film. This allows the inventive coating to be applied in an easier and less costly manner. Third, our inventive coating has a different chemical composition then the "PLAYTEX" "SILK GLIDE" coating. This different chemical composition allows our inventive coating to be applied in a single operation versus a dual operation. Fourth, our inventive coating gives an applicator a satiny finish, which is aesthetically pleasing in appearance, while the "PLAYTEX" "SILK GLIDE" coating gives an applicator a glossy finish. Lastly, our inventive coating can be applied to a single layer of paper to form an acceptable applicator while "PLAYTEX" has elected to apply their coating to an applicator formed from two layers of paper.

Referring again to FIG. 2, the applicator 10 is constructed of two slidable members and the outer surface of both the first member 22 and the second member 24 are coated. The first member 22 has coating 54 formed thereon and the second member 24 has a coating 56 formed thereon. Both coatings 54 and 56 are identical but they could be different if desired. The coating 56 on the second member 24 reduces the friction between the first and second members, 22 and 24 respectively. This is important because as a woman inserts the applicator into her vagina, she may actually squeeze the first member 22 such that its circular cross-section acquires an oval configuration. This change in geometry can significantly increase the frictional forces which are developed between the first and second members, 22 and 24 respectively. As the frictional force is increased, addition force is required to properly expel the tampon 12 from the outer tube 22.

Figure 5:
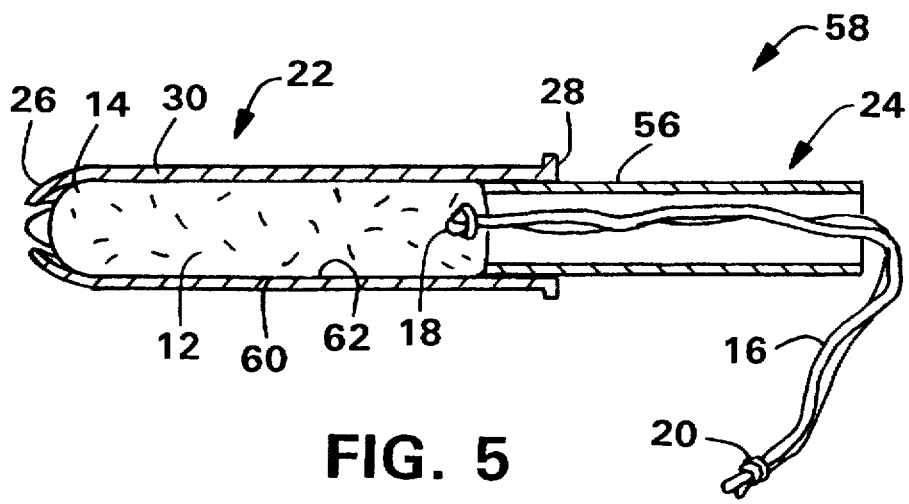
FIG. 5 is a cross-sectional view of a paper applicator depicting the presence of an outer tube having both the inner and outer surfaces coated and an inner tube having an outer surface which is coated.

Referring now to FIG. 5, another embodiment of an applicator 58 is shown wherein the paper layer 30 has an inner surface 60 which has a coating 62 formed thereon. The reference numerals in FIG. 5 are identical to those used in FIGS. 1 and 2 for similar components. By coating the inner surface 60 of the first member 22, one can be assured that the second member 24 will easily slide therein. To assure maximum performance, the outer surface of the second member 24 can also be coated so as to reduce the expulsion force needed to expel the tampon 12 from the first member 22.

APPARATUS

Figure 6:
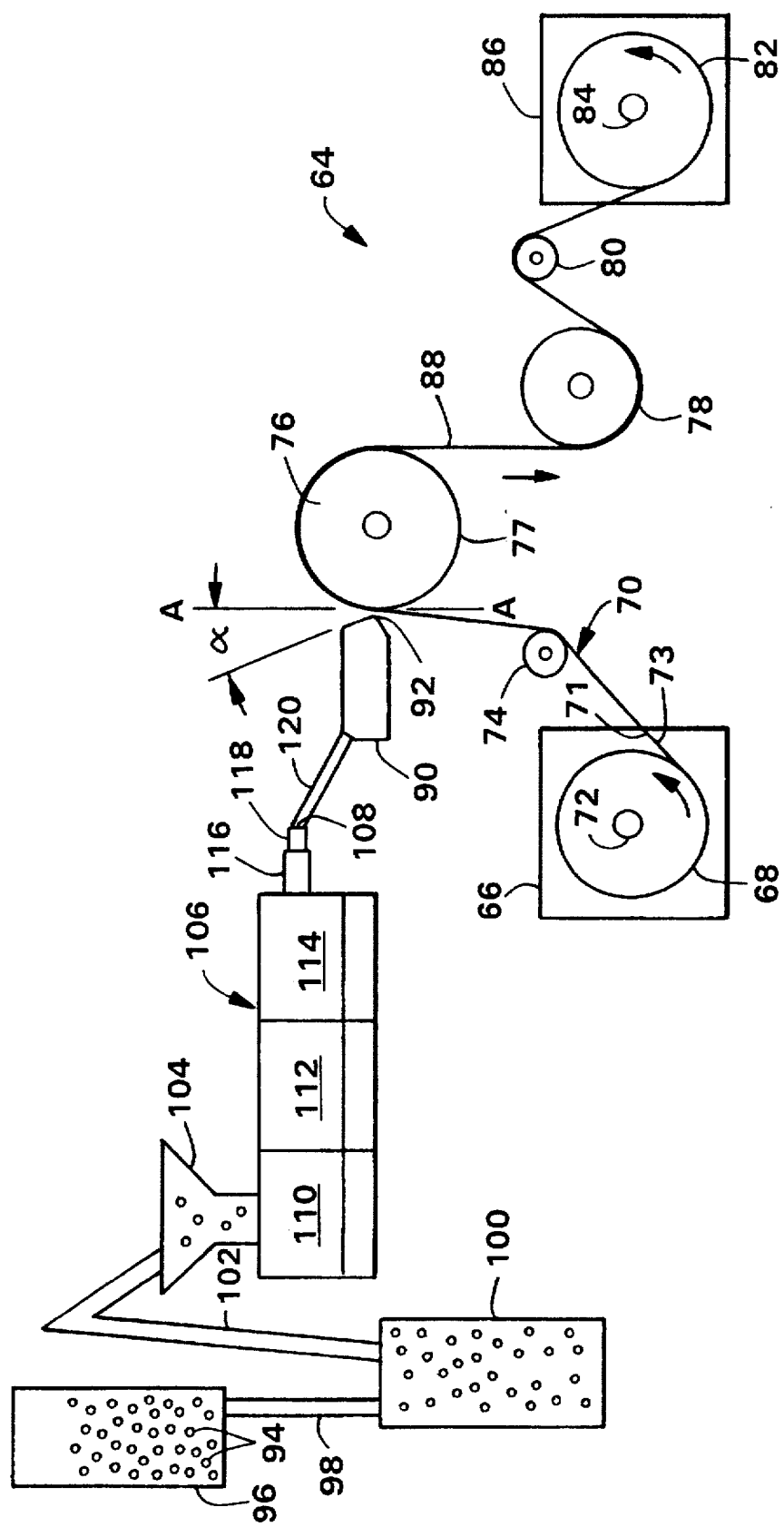
FIG. 6 is a schematic view of an apparatus used to slot coat a paper layer.

Referring to FIG. 6, an apparatus 64 which is useful for coating the paper applicator 10, 32 or 58 will now be taught. The apparatus 64 can vary depending upon the kind of paper which is to be coated as well as the final shape and size of the paper applicator. For most applicators, it is best to coat the layer of paper which will form the outer surface of the applicator before it is assembled into a tubular member. If one wished to coat the inner surface of the applicator as well, then the layer of paper which will form this surface should also be coated before assembly. It is also possible to vary the apparatus 64 slightly so that it can simultaneously coat the opposite major surfaces of a web of paper, if desired.

One expedient way of coating paper can be accomplished by using the apparatus 64. The apparatus 64 includes a first drive mechanism 66 which is capable of supporting a supply roll 68. The supply roll 68 holds a continuous strip of uncoated paper 70. By "continuous" is meant a finite amount of paper from which a plurality of applicators 10, 32 or 58 can be formed. The uncoated paper 70 contains two major surfaces 71 and 73. One or both of these major surfaces 71 and 73 can be coated either sequentially or simultaneously.

The first drive mechanism 66 supports a rotatable spindle 72. The supply roll 68 of uncoated paper 70 is mounted on the spindle 72 which can be driven at a predetermined speed by the first drive mechanism 66 or can be made to rotate by the force exerted on it by removing the uncoated paper 70. Before starting the apparatus 64, a leading edge of the uncoated paper 70 is first threaded over a first guide roll 74, a coating roll 76, a chill roll 78, a second guide roll 80 and is then attached to a take-up roll 82.

As is known to those skilled in the art, multiple guide rolls can be utilized on the apparatus 64 if necessary. Sometimes it is advantageous to arrange the guide rolls in pairs having a narrow nip formed therebetween. In FIG. 6, the guide rolls 74 and 80 are not used in a paired relationship.

The first guide roll 74 is positioned between the first drive mechanism 66 and the coating roll 76 and serves to properly align the strip of uncoated paper 70 which is unwound from the supply roll 68. It is important that the strip of paper 70 is properly oriented relative to the coating roll 76. The second guide roll 80 is positioned between the chill roll 78 and the second drive mechanism 86. Like the first guide roll 74, the second guide roll 80 also serves to properly align the strip of coated paper 98 so that it can be quickly and efficiently wound up on the take-up roll 82. The second guide roll 80 can be a variable bowed roll such as sold by Mount Hope, a division of BTR Paper Group having an office at 15 Fifth Street, Taunton, Mass. 02780.

The take-up roll 82 is coaxially mounted on a drive spindle 84 which is rotated by a second drive mechanism 86. The second drive mechanism 86 allows the coated paper 88 to be rewound onto the take-up roll 82 at a predetermined speed and under proper tension.

It has been found that a typical line speed using the apparatus 64 is from between about 100 feet per minute (fpm) to about 1200 fpm. A more preferred line speed is from between about 250 fpm to about 600 fpm, and the most preferable line speed is about 500 fpm. This line speed can vary depending upon the type of paper being coated, the particular composition of the liquid resin, the viscosity of the resin, the thickness of the coating, etc.

Referring back to the coating roll 76, it is beneficial to form a soft surface 77 on the outer periphery of the coating roll 76. This can be accomplished by coating or adhering a silicone rubber material onto the outer periphery of the coating roll 76. The soft surface 77 allows the strip of paper 70 to pass over the surface of the coating roll 76 with a minimum amount of slippage. The soft surface 77 also facilitates transfer of a predetermined amount of coating onto the uncoated paper 70 because it helps to control the nip opening formed with the associated coating mechanism.

The apparatus 64 also includes a slot coater 90 containing a slot die 92. The slot die 92 has an outer surface which is angularly aligned, ie., at an angle alpha, with the coating roll 76 such that a narrow opening or nip is present between the slot die 92 and the coating roll 76. This opening should be wide enough to allow the uncoated paper 70 to pass therethrough. An opening or nip of less than about 0.05 inches (about 1.3 mm), and preferably less than about 0.01 inches (about 0.25 mm) is sufficient for most applications wherein the thickness of the coating to be applied is less than 1.0 mils. The exact size of the opening can vary depending upon the thickness of the paper which is to be coated, the viscosity of the coating resin, the type of equipment one uses, the speed of the equipment, etc.

It should be noted that when the coated roll 76 has a soft surface 77, that an opening or nip may not be visually present because the coating roll 76 will abut the slot die 92. However, the soft surface 77 on the coating roll 76 is capable of being depressed so that the strip of paper 70 can pass between the slot die 92 and the coating roll 76.

A predetermined quantity of polylactide resin 94, in pellet form, is contained in a storage drum 96. The polylactide resin pellets are solid material which can vary in shape and form but normally have a cylindrical shape and are about ⅛ of an inch (about 3.18 mm) long. The solid pellets are routed via a supply conduit 98 to a sealed resin dryer 100. In the resin dryer 100, the solid pellets are elevated in temperature to drive off any moisture which may be present. The pellets are heated to a temperature ranging from between about 100° F. (about 38° C.) to about 150° F. (about 66° C.). A more preferred temperature to which the pellets are heated is about 130° F. (about 55° C.).

The dried heated pellets, still in solid form, are then routed via a conduit 102 to a sealed hopper 104 without being exposed to the atmosphere. It is important not to expose the pellets to the atmosphere to prevent additional moisture from contacting the pellets. From the sealed hopper 104 the pellets are gravity fed into an extruder 106. The extruder 106 contains an internal, elongated rotatable screw (not shown) which is designed to move the solid pellets which enter the extruder 106 from the hopper 104 through the extruder 106 and out an outlet 108 in a continuous stream of molten material. The extruder 106 also contains one or more heating zones in which the temperature is sequentially increased so as to transform the solid resin pellets into a molten material. In FIG. 6, the extruder 106 is depicted having three heating zones labeled 110, 112 and 114. The extruder could contain additional zones if desired.

In the first heating zone 110, the polylactide resin 94 is heated to a temperature of about 320° F. (about 160° C.). As the resin 94 is moved forward toward the outlet 108 by the internal screw, the resin will be transformed from a solid to a molten liquid. For example, in the second heating zone 112, the resin 94 is elevated to about 425° F. (about 218° C.) and in the third heating zone 114 the resin 94 is elevated to about 475° F. (about 246° C.). The exact temperature to which the resin 94 is heated to in each of the heating zones 110, 112 and 114 can vary depending upon one's equipment, the composition of the resin, the length of travel of the screw, etc.

After the third heating zone 114, the molten resin 94 passes through a throat 116 wherein it can be heated a few more degrees. For example, the polylactide resin 94 can be elevated to about 485° F. (about 252° C.) in the throat 116. At the outlet of the throat 116 is a filter 118 which can screen out any lumps or debris that may be present. Upon exiting the outlet 108 of the extruder 106, the molten polylactide resin passes through a hose 120 into the slot coater 90. In the slot coater 90 the temperature of molten resin is maintained and the resin is moved forward through the slot die 92 at a predetermined pressure. The liquid resin 94 is then dispensed in the form of a liquid stream or sheet of film through the slot die 92. The thickness of the liquid resin 94 applied to the uncoated paper 70 can be varied by the size and configuration of the opening formed in the slot die 92, as well as by the internal pressure exerted on the liquid resin 94 by the operation of the slot coater 90. As the liquid resin 94 is applied to the uncoated paper 70, the paper 70 becomes coated as is indicated by the numeral 88.

It should be noted that the outer surface of the slot die 92 can be aligned at an angle alpha (a) relative to the surface of the uncoated paper 70 which is to be contacted by the liquid resin 94. The angle alpha (a) can vary from between about 0° to about 10° relative to a vertical line A—A which is drawn tangential to the outer periphery of the coating roll 76 at a point where the uncoated paper 70 passes between the slot die 92 and the coating roll 76, see FIG. 6. Preferably, the angle alpha (a) is from between about 1° to about 5° relative to the vertical line A—A. More preferably, the angle alpha (a) is about 3° relative to the vertical line A—A. The purpose of angularly aligning the outer surface of the slot die 92 relative to the coating roll 76 is to obtain a smoother and more uniform transfer of the resin 94 onto the paper 70. This slight angular orientation accomplishes this function. It should be noted that those skilled in slot coating could interpret "the outer surface of the slot coater" to be the same as "the slot coater itself."

The temperature and viscosity of the liquid resin 94 can vary, however, for the coating composition described above, the temperature should range from between about 300° F. to about 400° F. (about 148° C. to about 204° C.). A temperature of from between about 310° F. to about 350° F. (about 154° C. to about 177° C.) is more preferred, and a temperature of about 325° F. (about 163° C.) is most preferred.

A uniform thickness of the liquid resin 94 should be deposited onto the continuous strip of paper 70 as it travels through the opening or nip formed between the slot die 92 and the coating roll 76. The thickness of the coating can be adjusted by varying the speed of the moving paper 70, the size of the opening formed in the slot die 92, the internal pressure exerted on the liquid resin 94, the viscosity of the resin 94, the temperature of the resin 94, etc. One or more of these parameters can be adjusted to precisely control the thickness of the coating which is applied to the coated paper 88.

After the molten resin 94 is deposited onto the passing paper 70, the coating is cooled by passing the paper 88 over the surface of the chill roll 78. The resin 94 is cooled to at least a partially solidified state. Preferably, the resin 94 is cooled to a solid consistency before it is rolled up on the take-up roll 82. One or more sequentially arranged chill rolls can be utilized to more efficiently cool the resin 94. In FIG. 6, only one chill roll 78 is depicted. The chill roll 78 can be cooled by water or by another type of commercially available coolant. It is most efficient to the process when the chill roll 78 is maintained at a temperature of less than about 100° F. (about 38° C). Preferably, the chill roll 78 is maintained at a temperature of from between about 40° F. to about 80° F. (about 5° C. to about 27° C.). More preferably, the chill roll 78 is maintained at a temperature of from between about 50° F. to about 75° F. (about 10° C. to about 24° C.), and most preferably, the chill roll 78 is maintained at a temperature below about 70° F. (about 21° C.). The exact temperature below 100° F., at which the chill roll 78 is maintained, will be dictated by one's particular equipment, operating speeds, type of resin, temperature of the resin, etc.

It should also be noted that the coating roll 76 can also be chilled or maintained at room temperature so as to assist the chill roll 78 in cooling the hot resin 94. Furthermore, one may employ other means of cooling the hot resin 94, such means being known to those skilled in the art. After being cooled, the coated paper 88 is directed to and rolled up on the take-up roll 82.

It should be noted that if one desired to coat both major surfaces 71 and 73 of the strip of paper 70 simultaneously, that this is possible. This can be accomplished by installing a second slot coater and a second coating roll adjacent to the first slot coater 90. Other variations can also be made to the apparatus 64 to suit one's particular requirements. Alternatively, one can run the coated strip of paper 88 back through the apparatus 64 and coat the uncoated surface 73 to obtain a strip of paper which is coated on both major surfaces 71 and 73.

METHOD

Figure 7:
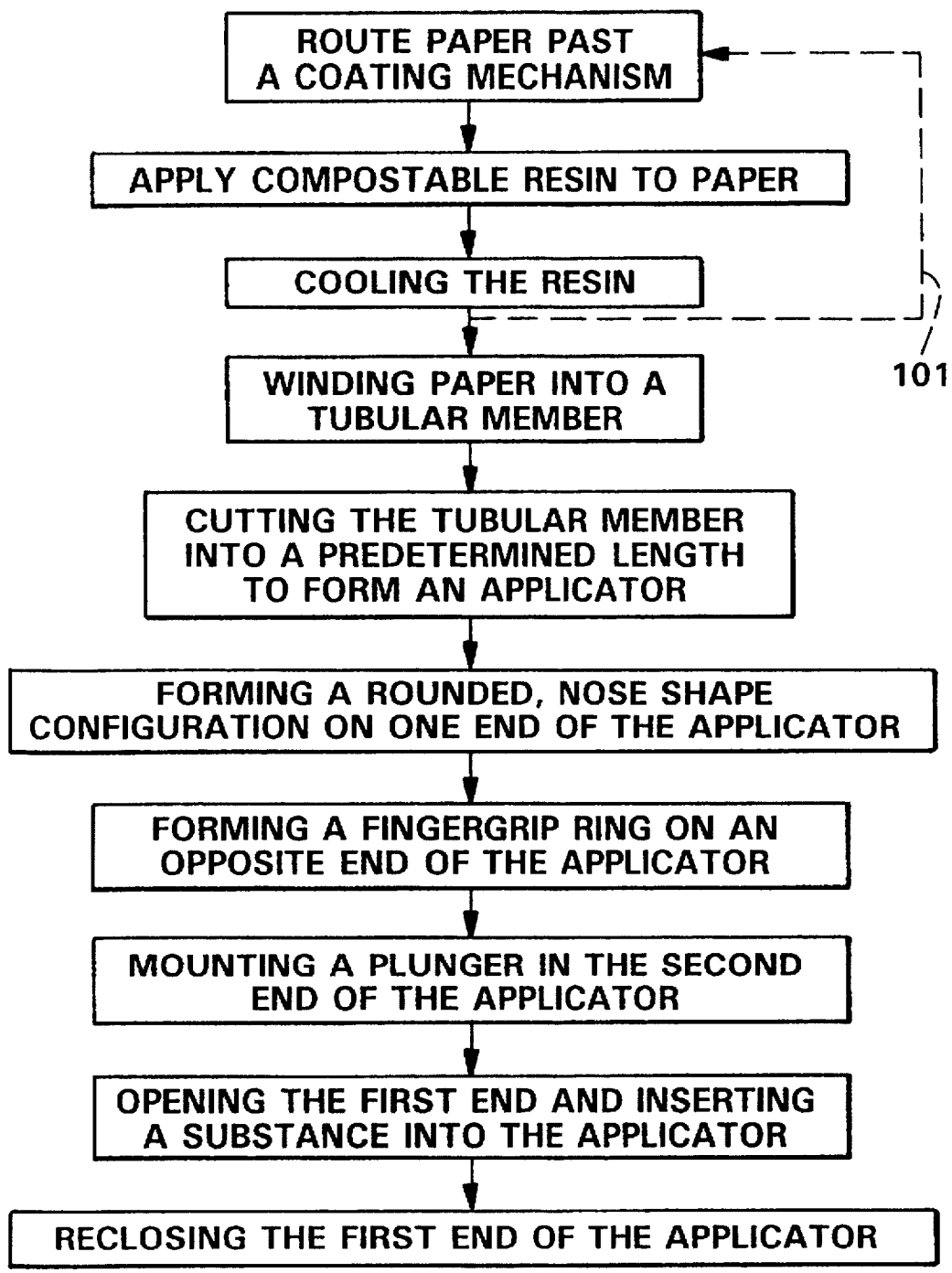
FIG. 7 is a flow diagram of a method used to form a paper applicator having a coating applied to a surface thereof.

Referring to FIG. 7, a flow diagram is depicted which illustrates a method of coating one or more layers of paper 70 and then forming the coated paper 88 into a tampon applicator 10, 32 or 58. The method includes the steps of routing a strip of uncoated paper 70 past a coating mechanism 90. The paper 70, which can be unrolled from a supply roll 68, is in the form of a continuous strip or ribbon. The strip of paper 70 has a pair of oppositely aligned major surfaces 71 and 73. A single layer of compostable, molten thermoplastic resin 94 is applied onto at least one of the major surfaces 71 and/or 73 of the paper 70 to form a strip of coated paper 88. The resin 94 is normally applied to the strip of paper 70 at a temperature of from between about 400° F. to about 500° F. (about 204° C. to about 260° C.). The resin 94 can be applied to only one major surface 71 or 73 or onto both major surfaces 71 and 73. Whether one coats one or both major surfaces 71 and/or 73 of the strip of paper 70 depends upon whether one desires the finished article to be coated on only an interior surface 60 or an exterior surface 52 or if one desires to have both surfaces coated 52 and 60, see FIGS. 2 and 5. One way of applying a uniform coating of resin 94 onto the strip of paper 70 is by slot coating.

The method further includes cooling the hot resin 94 into at least a partially solidified state. The resin 94 can be cooled to a temperature of from between about 40° F. to about 100° F. (about 5° C. to about 38° C.). Alternatively, the resin 94 can be cooled down to room temperature.

When one wishes to coat both major surfaces 71 and 73 of the strip of paper 70 in a sequential operation, one can route the paper 88, which is coated on the one surface 71, back through the coating mechanism. This procedure is indicated by the dotted line labeled 100 in FIG. 7. Alternatively, the strip of uncoated paper 70 can be coated on both major surfaces 71 and 73 by two slot coaters arranged downstream of one another.

After the resin 94 has at least partially, and preferably completely, solidified the strip of coated paper 88 is wound up into a hollow tubular member. If it is desirable to have the coating appear on the exterior surface of the article, the strip of coated paper 88 is wound such that the coating will appear on the exterior surface. The tubular member can consist of a single layer of coated paper 88 or it can be constructed from two or more layers of paper, paperboard, cardboard or some other material such as a thermoplastic film wherein at least one layer is coated on at least one surface. The use of two or more layers is beneficial in giving the applicator 10, 32 or 58 the required rigidity or its intended purpose. When more than one layer is required, the strip of coated paper 88 can be adhesively attached to one or more layers of similar or different materials. The strip of coated paper 88 should be attached to the other layers such that the coated surface appears on either the exterior surface or the interior surface of the finished applicator. If both the exterior surface and the interior surface have to be coated, then two strips of coated paper will be required to form the finished applicator.

It should be noted that when an applicator 58 is to be constructed from a single layer of paper and both the interior and exterior surfaces of an applicator are to be coated, that this can be obtained by coating both surfaces of the strip of paper 70. The coated paper 88 is then rolled, winded or longitudinally seamed into a tubular configuration.

It is possible to wind the strip of coated paper 88 parallel to its length to form an elongated, hollow tubular member. This tubular member can then be cut into predetermined lengths to form applicators having first and second ends. Alternatively, the strip of coated paper 88 can be cut into individual segments which are then rolled, wound or longitudinally seamed into hollow, tubular members. In this alternative process, each tubular member can be wound either parallel or perpendicular to the initial length of the strip of paper. It is also possible to convolutely or spirally wind the coated paper 88 at an angle relative to the initial length of the strip of paper.

Once the strip of paper is wound into a tubular member, the paper is sealed or bonded together to retain its shape and form the applicator. This can be accomplished several ways including using an adhesive or glue, by ultrasonic bonding, by bonding with heat or pressure or by bonding with both heat and pressure, or by other means known to those skilled in the art.

For some applicators, it will not be necessary to configure one or both ends in order to facilitate expulsion of the substance therefrom. However, for tampon applicators in particular, it is advantageous to the smooth and comfortable operation of the applicator that at least one end of the applicator be conformed into a particular shape. In the case of a tampon applicator, the first end of the applicator is formed into an approximately rounded, nose-shaped configuration. This rounded configuration can be semi-circular, frusto-conical or tapering as viewed in a side profile. The normally smaller diameter, rounded tip facilitates comfortable insertion of the applicator into a woman's vagina. Along with configuring the first end of the applicator, the second end can also be worked or formed into a fingergrip ring simultaneously or sequentially. It should be noted that the second end of the applicator can be formed before forming the first end if desired. The fingergrip ring aids the user by providing a surface which acts as a stop for her fingers. The fingergrip ring will prevent her fingers from sliding off of the exterior surface of the applicator as she pushes inward on the plunger to expel the tampon into her vagina.

For a two piece applicator, a plunger is telescopically mounted in the second end of the outer tube, see FIGS. 1 and 2. The first end of the applicator is then opened and a substance, such as a tampon, is inserted therein. The first end is then reclosed. The applicator is now ready to facilitate dispersion of the substance into a body cavity or onto the surface of the skin. This is accomplished by pushing the plunger into the applicator and causing the substance or tampon to be expelled out of the first end of the applicator.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An applicator comprising:
 a) a tubular member formed from a single layer of paper and having an exterior surface, said tubular member capable of holding a substance which is to be inserted into a body cavity; and
 b) a coating applied to said exterior surface, said coating being a single layer of a compostable material and comprising at least 85 percent by weight of a polylactide polymeric material, at least 10 percent by weight of additives, and up to about 5 percent by weight of a residual monomer, wherein said coating provides said tubular member with a dry coefficient of kinetic friction value ranging from between 0.62 to 0.86.

2. The applicator of claim 1 wherein said single layer comprising at least 85 percent by weight of polylactide polymeric material has a thin uniform thickness formed by slot coating.

3. The applicator of claim 2, wherein said tubular member has an insertion end and has flexible petals on said insertion end.

4. The tampon applicator of claim 1 wherein said additives include a nucleating agent comprising adipic acid, an anti-oxidant or stabilizer, a plasticizer, an anti-blocking agent, a slip agent and a water scavenger.

5. The tampon applicator of claim 4 wherein said nucleation agent is present in said coating in an amount ranging from between about 1 to about 5 percent by weight.

6. A tampon applicator comprising:
 a) at least one elongated tubular member formed from at least one layer of paper and having an exterior surface; and
 b) a coating applied to said exterior surface of said tubular member, said coating being a single layer of a compostable material and said coating comprising at least 85 percent by weight of polylactide, at least 10 percent by weight of additives, and up to about 5 percent by weight of a residual monomer, said coating providing said tubular member with a dry coefficient of kinetic friction ranging from between 0.62 to 0.86, wherein said coating has a uniform thickness.

7. The tampon applicator of claim 6 wherein said coating has a uniform thickness which does not vary over plus or minus 15 per cent over said exterior surface.

8. The tampon applicator of claim 6 wherein said coating has a thickness of from between about 0.3 to about 1.0 mils.

9. The tampon applicator of claim 6 wherein said additive includes a plasticizer in an amount of from between about 6 to about 15 percent by weight.

10. The tampon applicator of claim 6 wherein said additive includes an anti-oxidant in an amount of from between about 1 to about 5 percent by weight.

11. A tampon applicator comprising:
 a) an elongated tubular member formed from at least two layers of paper, said tubular member having an exterior surface; and
 b) means for providing a specific dry coefficient of kinetic friction and a specific wet coefficient of kinetic friction to said tubular member and for facilitating insertion of said tubular member into said body cavity, said specific dry coefficient of kinetic friction having a value ranging from between 0.62 to 0.86 and said specific wet coefficient of kinetic friction having a value ranging from between 0.69 to 1.12, said means being applied to said exterior surface of said tubular member, said means forming a single layer of a compostable material and said means comprising at least 85 percent by weight of polylactide, at least 10 percent by weight of additives, and up to about 5 percent of a residual monomer, said additives including a nucleating agent, an anti-oxidant or stabilizer, a plasticizer, an anti-blocking agent, a slip agent and a water scavenger.

12. The tampon applicator of claim 11 wherein said means for providing a specific dry coefficient of kinetic friction and a specific wet coefficient of kinetic friction to said tubular member and for facilitating insertion has a thickness of less than about 1 mil.

13. The tampon applicator of claim 11 wherein said means for providina a specific dry coefficient of kinetic friction and a specific wet coefficient of kinetic friction to said tubular member and for facilitating insertion provides a dry coefficient of kinetic friction value of less than 0.80.

14. The tampon applicator of claim 11 wherein said means for providing a specific dry coefficient of kinetic friction and a specific wet coefficient of kinetic friction to said tubular member and for facilitating insertion provides a wet coefficient of kinetic friction value of less than 1.0.

15. The tampon applicator of claim 11 wherein said additive includes a nucleating agent of adipic acid in an amount of from between about 1 to about 5 percent by weight.

16. The tampon applicator of claim 11 wherein said additive includes an anti-oxidant in an amount of from between about 1 to about 5 percent by weight.

17. The tampon applicator of claim 11 wherein said additive includes a plasticizer in an amount of from between about 6 to about 15 percent by weight.

18. The tampon applicator of claim 11 wherein said additive includes an anti-blocking agent in an amount of from between about 0.5 to about 10 percent by weight.

19. The tampon applicator of claim 11 wherein said additive includes a slip agent in an amount of from between about 1 to about 5 percent by weight.

20. The tampon applicator of claim 11 wherein said additive includes a water scavenger in an amount of from between about 0.5 to about 5 percent by weight.

21. An applicator comprising:
 a) a tubular member formed from a single layer of paper and having an interior surface and an exterior surface, said tubular member capable of holding a substance which is to be inserted into a body cavity; and
 b) a coating applied to said interior surface and said exterior surface of said tubular member, said coating being a single layer of a compostable material and said coating comprising at least 85 percent by weight of a polylactide polymeric material, at least 10 percent by weight of additives, and from about 0.1 to about 5 percent by weight of a residual monomer, said additives including a nucleating agent, an anti-oxidant or stabilizer, a plasticizer, an anti-blocking agent, a slip agent and a water scavenger.

22. The applicator of claim 21 wherein said coating applied to said exterior surface provides said tubular member with a dry coefficient of kinetic friction value ranging from between 0.62 to 0.86.

23. A tampon applicator comprising:
 a) at least one elongated tubular member formed from at least one layer of paper and having an interior surface; and b) a coating applied to said interior surface of said tubular member, said coating being a single layer of a compostable material and said coating comprising at least 85 percent by weight of polylactide, at least 10 percent by weight of additives, and from about 0.1 to about 5 percent by weight of a residual monomer, said coating providing said tubular member with a dry coefficient of kinetic friction ranging from between 0.62 to 0.86 and a wet coefficient of kinetic friction ranging from between 0.69 to 1.12, and said low dry and wet coefficient of kinetic friction values facilitating insertion of said applicator into said body cavity.

24. A tampon applicator comprising:

a) an elongated tubular member formed from at least two layers of paper, said tubular member having an interior surface; and b) a coating applied to said interior surface of said tubular member, said coating being a single layer of a compostable material and said coating comprising at least 85 percent by weight of polylactide, at least 10 percent by weight of additives, and from about 0.1 to about 5 percent by weight of a residual monomer, said coating having a thickness of less than about 0.7 mils and said coating providing said tubular member with a dry coefficient of kinetic friction ranging from between 0.62 to 0.86 and a wet coefficient of kinetic friction ranging from between 0.69 to 1.12, and said low dry and wet coefficient of kinetic friction values facilitating insertion of said applicator into said body cavity.

* * * * *